(12) United States Patent
Young et al.

(10) Patent No.: US 8,103,241 B2
(45) Date of Patent: Jan. 24, 2012

(54) METHOD AND SYSTEM FOR WIRELESS DEVICE COMMUNICATION

(75) Inventors: Morris J. Young, Indianapolis, IN (US); Christopher Richard Baker, Fishers, IN (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 1081 days.

(21) Appl. No.: 11/999,879

(22) Filed: Dec. 7, 2007

(65) Prior Publication Data

US 2009/0149131 A1    Jun. 11, 2009

(51) Int. Cl.
*H04M 11/04*   (2006.01)

(52) U.S. Cl. .......... 455/404.1; 455/3.06; 455/404.2; 455/412.1; 340/825.49

(58) Field of Classification Search .......... 455/404.1, 455/3.06, 404.2, 412.2, 41.2, 521, 67.11; 600/508; 340/825.49
See application file for complete search history.

(56) References Cited

U.S. PATENT DOCUMENTS

| | | | |
|---|---|---|---|
| 4,731,726 A | 3/1988 | Allen, III | |
| 4,945,244 A | 7/1990 | Castleman | |
| 5,241,410 A * | 8/1993 | Streck et al. | 398/115 |
| 5,251,126 A | 10/1993 | Kahn et al. | |
| 5,338,157 A | 8/1994 | Blomquist | |
| 5,376,070 A | 12/1994 | Purvis et al. | |
| 5,396,224 A * | 3/1995 | Dukes et al. | 340/539.13 |
| 5,540,235 A * | 7/1996 | Wilson | 600/554 |
| 5,658,250 A | 8/1997 | Blomquist et al. | |
| 5,665,065 A | 9/1997 | Colman et al. | |
| 5,795,327 A | 8/1998 | Wilson et al. | |
| 5,808,285 A * | 9/1998 | Rockstein et al. | 235/472.02 |
| 5,811,786 A * | 9/1998 | Rockstein et al. | 235/472.01 |
| 5,954,641 A | 9/1999 | Kehr et al. | |
| 6,024,699 A | 2/2000 | Surwit et al. | |
| 6,068,615 A | 5/2000 | Brown et al. | |
| 6,102,855 A | 8/2000 | Kehr et al. | |
| 6,110,148 A | 8/2000 | Brown et al. | |
| 6,113,578 A | 9/2000 | Brown | |
| 6,211,790 B1 * | 4/2001 | Radomsky et al. | 340/573.4 |
| 6,241,704 B1 | 6/2001 | Peterson et al. | |
| 6,314,405 B1 | 11/2001 | Richardson | |
| 6,322,502 B1 | 11/2001 | Schoenberg et al. | |
| 6,368,272 B1 | 4/2002 | Porumbescu | |
| 6,409,675 B1 * | 6/2002 | Turcott | 600/508 |
| 6,427,088 B1 | 7/2002 | Bowman, IV et al. | |
| 6,544,212 B2 | 4/2003 | Galley et al. | |
| 6,545,643 B1 | 4/2003 | Sward et al. | |
| 6,551,276 B1 | 4/2003 | Mann et al. | |

(Continued)

FOREIGN PATENT DOCUMENTS

EP    0 699 046    9/1996

(Continued)

OTHER PUBLICATIONS

Cabri et al.; "*Agent-based Plug-and-Play Integration of Role-Enabled Medical Devices*", IEEE Computer Society, Aug. 2007, p. 111-121.

(Continued)

*Primary Examiner* — Minh D Dao
(74) *Attorney, Agent, or Firm* — Baker & Daniels LLP

(57) ABSTRACT

A medical data receiver configured to wirelessly receive medical data via a signal and having an externally perceptible indicator of signal reception.

17 Claims, 4 Drawing Sheets

U.S. PATENT DOCUMENTS

| | | | |
|---|---|---|---|
| 6,558,320 B1 | 5/2003 | Causey, III et al. | |
| 6,562,001 B2 | 5/2003 | Lebel et al. | |
| 6,564,105 B2 | 5/2003 | Starkweather et al. | |
| 6,571,128 B2 | 5/2003 | Lebel et al. | |
| 6,577,899 B2 | 6/2003 | Lebel et al. | |
| 6,585,644 B2 | 7/2003 | Lebel et al. | |
| 6,605,038 B1 | 8/2003 | Teller et al. | |
| 6,635,014 B2 | 10/2003 | Starkweather et al. | |
| 6,648,821 B2 | 11/2003 | Lebel et al. | |
| 6,659,948 B2 | 12/2003 | Lebel et al. | |
| 6,668,196 B1 | 12/2003 | Villegas et al. | |
| 6,687,546 B2 | 2/2004 | Lebel et al. | |
| 6,694,191 B2 | 2/2004 | Starkweather et al. | |
| 6,714,724 B1 | 3/2004 | Cook | |
| 6,733,446 B2 | 5/2004 | Lebel et al. | |
| 6,740,075 B2 | 5/2004 | Lebel et al. | |
| 6,752,787 B1 | 6/2004 | Causey, III et al. | |
| 6,753,781 B2* | 6/2004 | Radomsky et al. | 340/573.4 |
| 6,758,810 B2 | 7/2004 | Lebel et al. | |
| 6,781,522 B2 | 8/2004 | Sleva et al. | |
| 6,804,656 B1 | 10/2004 | Rosenfeld et al. | |
| 6,809,653 B1 | 10/2004 | Mann et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,852,104 B2 | 2/2005 | Blomquist | |
| 6,873,268 B2 | 3/2005 | Lebel et al. | |
| 6,912,379 B2* | 6/2005 | Horng | 455/226.4 |
| 6,958,705 B2 | 10/2005 | Lebel et al. | |
| 6,988,026 B2* | 1/2006 | Breed et al. | 701/29 |
| 7,020,508 B2 | 3/2006 | Stivoric et al. | |
| 7,024,236 B2 | 4/2006 | Ford et al. | |
| 7,029,455 B2 | 4/2006 | Flaherty | |
| 7,039,703 B1 | 5/2006 | Clancy et al. | |
| 7,041,468 B2 | 5/2006 | Drucker et al. | |
| 7,063,665 B2 | 6/2006 | Hasegawa et al. | |
| 7,072,356 B1 | 7/2006 | Clancy et al. | |
| 7,082,334 B2 | 7/2006 | Boute et al. | |
| 7,103,460 B1* | 9/2006 | Breed | 701/29 |
| 7,120,488 B2 | 10/2006 | Nova et al. | |
| 7,165,062 B2 | 1/2007 | O'Rourke | |
| 7,179,226 B2 | 2/2007 | Crothall et al. | |
| 7,181,350 B2 | 2/2007 | Oberding et al. | |
| 7,734,476 B2* | 6/2010 | Wildman et al. | 705/2 |
| 2002/0016568 A1 | 2/2002 | Lebel et al. | |
| 2002/0029776 A1 | 3/2002 | Blomquist | |
| 2002/0040208 A1 | 4/2002 | Flaherty et al. | |
| 2002/0094778 A1 | 7/2002 | Cannon et al. | |
| 2002/0193679 A1 | 12/2002 | Malave et al. | |
| 2003/0011646 A1 | 1/2003 | Levine et al. | |
| 2003/0060765 A1 | 3/2003 | Campbell et al. | |
| 2003/0065308 A1 | 4/2003 | Lebel et al. | |
| 2003/0065536 A1 | 4/2003 | Hansen et al. | |
| 2003/0163088 A1 | 8/2003 | Blomquist | |
| 2003/0163789 A1 | 8/2003 | Blomquist | |
| 2004/0073464 A1 | 4/2004 | Huang | |
| 2004/0119742 A1 | 6/2004 | Silbey et al. | |
| 2004/0172284 A1 | 9/2004 | Sullivan et al. | |
| 2004/0193449 A1* | 9/2004 | Wildman et al. | 705/2 |
| 2004/0235446 A1 | 11/2004 | Flaherty et al. | |
| 2004/0254434 A1 | 12/2004 | Goodnow et al. | |
| 2004/0260233 A1 | 12/2004 | Garibotto et al. | |
| 2005/0004947 A1 | 1/2005 | Emlet et al. | |
| 2005/0022274 A1 | 1/2005 | Campbell et al. | |
| 2005/0137653 A1 | 6/2005 | Friedman et al. | |
| 2005/0192844 A1 | 9/2005 | Esler et al. | |
| 2006/0074462 A1 | 4/2006 | Verhoef | |
| 2006/0167367 A1 | 7/2006 | Stanczak et al. | |
| 2006/0209745 A1 | 9/2006 | MacMullan et al. | |
| 2006/0216011 A1* | 9/2006 | Godehn | 396/58 |
| 2006/0248398 A1 | 11/2006 | Neel et al. | |
| 2006/0279431 A1 | 12/2006 | Bakarania et al. | |
| 2007/0033074 A1 | 2/2007 | Nitzan et al. | |
| 2007/0048691 A1 | 3/2007 | Brown | |
| 2007/0179352 A1 | 8/2007 | Randlov et al. | |
| 2007/0219432 A1 | 9/2007 | Thompson | |
| 2007/0253021 A1 | 11/2007 | Mehta et al. | |
| 2007/0276197 A1 | 11/2007 | Harmon | |
| 2008/0001735 A1* | 1/2008 | Tran | 340/539.22 |
| 2008/0107274 A1* | 5/2008 | Worthy | 380/278 |
| 2009/0156924 A1* | 6/2009 | Shariati et al. | 600/365 |
| 2009/0192751 A1* | 7/2009 | Kamath et al. | 702/104 |
| 2010/0124920 A1* | 5/2010 | Feher | 455/426.1 |
| 2010/0228977 A1* | 9/2010 | Sievert et al. | 713/168 |

FOREIGN PATENT DOCUMENTS

| | | |
|---|---|---|
| EP | 0 970 655 | 1/2000 |
| EP | 0 649 316 B1 | 12/2000 |
| EP | 1 194 864 A2 | 4/2002 |
| EP | 1 502 614 | 2/2005 |
| EP | 1 722 310 | 4/2005 |
| WO | WO9728736 | 2/1997 |
| WO | WO9935856 | 12/1998 |
| WO | WO0200111 | 1/2000 |
| WO | WO0018449 | 2/2000 |
| WO | WO0072181 | 11/2000 |
| WO | WO02078512 | 10/2002 |
| WO | WO03015838 | 2/2003 |
| WO | WO2004090661 | 10/2004 |
| WO | WO2005011249 | 2/2005 |
| WO | WO2005037095 | 4/2005 |
| WO | WO2005096206 | 10/2005 |
| WO | WO2005114534 | 12/2005 |
| WO | WO2005114535 | 12/2005 |
| WO | WO2006050485 | 2/2006 |
| WO | WO2006108858 | 10/2006 |
| WO | WO2006118763 | 11/2006 |
| WO | WO2007051139 | 5/2007 |
| WO | WO2007093482 | 8/2007 |
| WO | WO2008147567 | 12/2008 |

OTHER PUBLICATIONS

"*The HAVi Specification—Specification of the Home Audio/Video Interoperability (HAVi) Architecture*," Nov. 19, 1998, pp. 1-409, Version 1.0 beta.

Hotchkiss et al.; "MD-Adapt a Proposed Architecture for Open-Source Medical Device Interoperability", 2007, IEEE Computer Society, Aug. 2007, pp. 167-169.

"CoPilot Health Management System Version 3.1," User's Guide, Mar. 2007, 230 pp., ART 10641 Rev. D, Abbott Diabetes Care, Inc.

"MediSense® Precision Link® Diabetes Data Management Software," User's Guide, May 2006, 58 pp., 116-412 Rev. AC, Abbott Diabetes Care, Inc.

Albisser, Michael A.; "A Graphical User Interface for Diabetes Management Than Integrates Glucose Prediction and Decision Support," Diabetes Technology & Therapeutics, 2005, pp. 264-273, vol. 7, No. 2.

Janssen et al., "Acensia® Winglucofacts® Professional Intelligent Diabetes Management Software Is an Effective Tool for the Management of Diabetes," Bayer HealthCare Clinical Summary Report, Jul. 2005, 10 pp.

Joshy et al.; "Diabetes Information Systems: A Rapidly Emerging Support for Diabetes Surveillance and Care," Diabetes Technology & Therapeutics, 2006, pp. 587-597, vol. 8, No. 5.

"OneTouch Diabetes Management Software," User Manual, 2006, 173 pp., v. 2.3.1, Lifescan, Inc.

"Getting Started, CareLink Personal Therapy Management Software for Diabetes," Brochure, 2007, 20 pp., Medtronic Minimed, Inc.

"Accu-Chek® Camit Pro Diabetes Management Software," User's Manual, 2005, 220 pp., v.2.1 and Addendum v. 2.4, Roche Diagnostics Corp.

"Accu-Chek® Compass Diabetes Care Software," User's Guide, 2005, 74 pp., Roche Diagnostics Corp.

"Accu-Chek® Diabetes Assistant," accessed with notional data and printed from www.diabetesassistant.com on Jan. 16, 2007, 20 pp., Roche Diagnostics Corp.

Partial International Search Report on Patentability for PCT/EP2008/009868 issued by the European Patent Office (3 pages).

* cited by examiner

METHOD AND SYSTEM FOR WIRELESS DEVICE COMMUNICATION

FIELD OF THE INVENTION

The present disclosure relates to a method and system for managing health data. More particularly, the disclosure relates a method and system for interfacing with a medical device.

BACKGROUND OF THE INVENTION

Many fields of medical treatment and healthcare require monitoring of certain body functions, physical states and conditions, and patient behaviors. Thus, e.g., for patients suffering from diabetes, a regular check of the blood glucose level forms an essential part of the daily routine. The blood glucose level has to be determined quickly and reliably, often several times per day. Medical devices are used to facilitate the collection of medical information without unduly disturbing the lifestyle of the patient. A large number of medical devices for monitoring various body functions are commercially available. Also, medical treatment and healthcare may require monitoring of exercise, diet, meal times, stress, work schedules and other activities and behaviors.

To reduce the frequency of necessary visits to doctors, the idea of home care gained popularity over the recent years. Technological advancements in medicine led to the increased use of medical devices. Many of these medical devices, such as meters and medicine delivery devices, are able to collect and store measurements and other data for long periods of time. Other devices, such as computers, portable digital assistants (PDAs), and cell phones, have been adapted to medical uses by the development of software directed to the collection of healthcare data. These advancements led to the development of health management systems that enable collection and use of large numbers of variables and large amounts of healthcare data. While systems were traditionally developed for use in healthcare facilities and health management organizations including insurance companies and govermnental agencies (HCP systems), increased technological sophistication by the populous at large led to the increased use of health management systems by patients, care givers, and others (patient systems) in addition to increased use by HCP systems. U.S. Pat. No. 7,103,578 and U.S. Published Application No. 2004/0172284 disclose two such methods and systems. Many of these systems are able to transfer data between them. Patient healthcare data is often transferred from a patient system to an HCP system. HCP systems may transfer remarks and other data to patient systems or other HCP systems.

SUMMARY OF THE INVENTION

The disclosure relates to a method and system for interfacing between a healthcare management system and medical devices. One embodiment of the system includes a medical data transmission system. The system includes a dongle configured to wirelessly receive medical data via a signal and including an externally perceptible indicator of the strength of signal reception, and a medical device configured to generate data indicative of a health condition and being capable of generating the signal.

In another embodiment, a computer readable medium is provided. The computer readable medium including operating instructions thereon such that when interpreted by a processor cause the processor to perform the step of automatically loading interface instructions upon startup of the processor. The interface instructions, when interpreted by the processor cause the processor to perform the steps of: automatically wirelessly downloading medical information from a medical data device; and storing the medical information in a database.

In yet another embodiment, a medical data transmission system is provided including: a transceiver configured to wirelessly receive medical data from a medical device via a data signal; the transceiver emitting a beacon signal detectable by the medical device.

In still another embodiment, a medical data transmission system is provided including a medical data device configured to wirelessly communicate medical data to a receiver via a data signal in an active state; the medical device having a listening mode in which the device monitors for a beacon signal emitted by the receiver.

BRIEF DESCRIPTION OF THE DRAWINGS

For more complete understanding of the present disclosure, reference is established to the following drawings in which.

Figure 1:
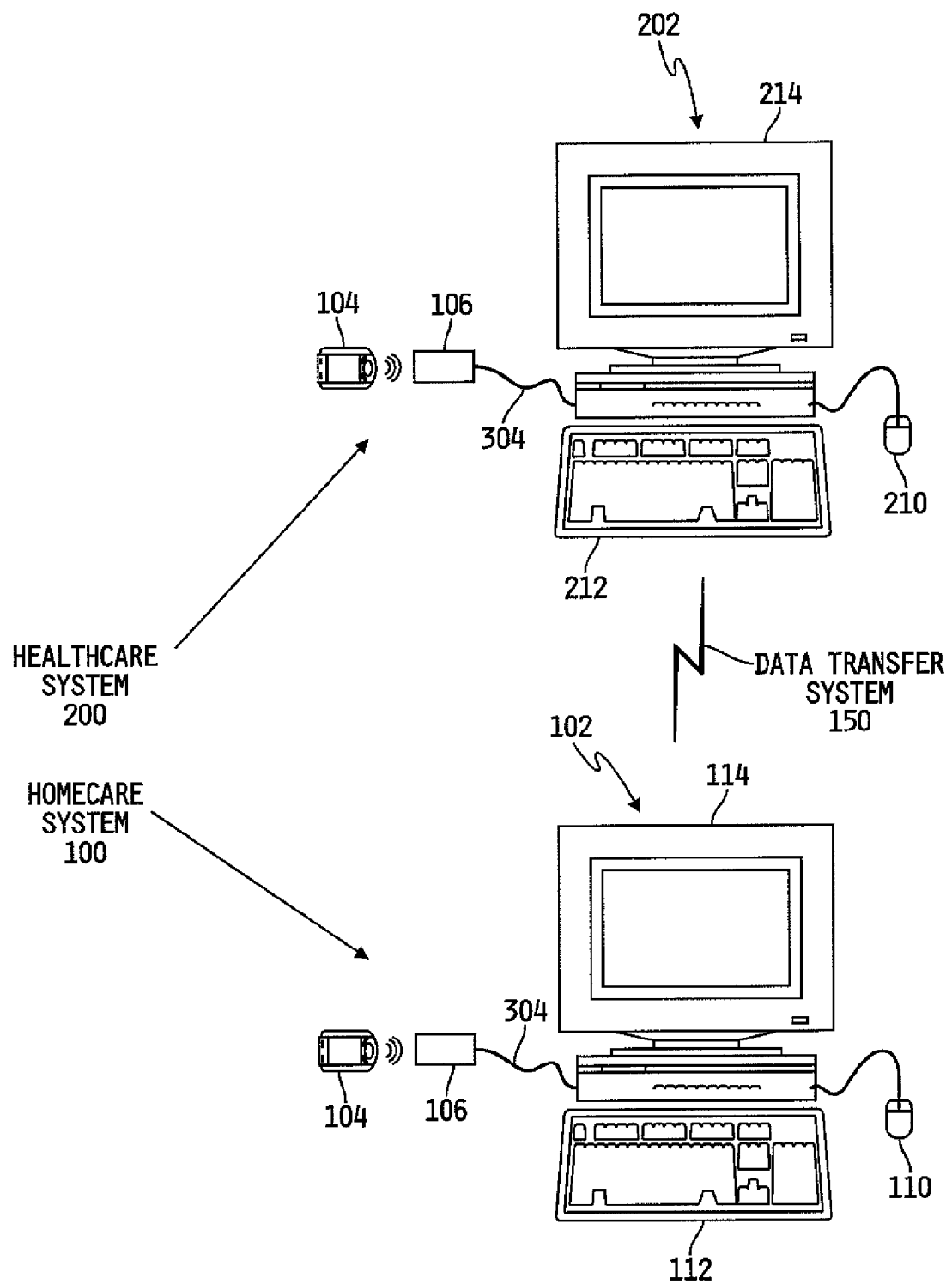
FIG. 1 shows an embodiment of a health management system comprising a healthcare system and a homecare system.

Corresponding reference characters indicate corresponding parts throughout the several views. Although the drawings represent embodiments of various features and components according to the present invention, the drawings are not necessarily to scale and certain features may be exaggerated in order to better illustrate and explain the present invention. The exemplification set out herein illustrates embodiments of the invention, and such exemplifications are not to be construed as limiting the scope of the invention in any manner.

DETAILED DESCRIPTION OF EMBODIMENTS OF THE INVENTION

For the purposes of promoting an understanding of the principles of the disclosure, reference will now be made to the embodiments illustrated in the drawings, which are described below. The embodiments disclosed below are not intended to be exhaustive or limit the disclosure to the precise form disclosed in the following detailed description. Rather, the embodiments are chosen and described so that others skilled in the art may utilize their teachings. It will be understood that no limitation of the scope of the invention is thereby intended. The disclosure includes any alterations and further modifications in the illustrated devices and described methods and further applications of the principles of the disclosure which would normally occur to one skilled in the art to which the disclosure relates.

The terms "network," "local area network," "LAN," "wide area network," or "WAN" mean two or more computers which are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks can access the network resources, such as shared data files, common peripheral devices, and inter-workstation communication. The computers have at least one processor for executing machine instructions, and memory for storing instructions and other information. Many combinations of processing circuitry and information storing equipment are known by those of ordinary skill in these arts. A processor may be a microprocessor, a digital signal processor ("DSP"), a central processing unit ("CPU"), or other circuit or equivalent capable of interpreting instructions or performing logical actions on information. Memory includes both volatile and non-volatile memory, including temporary and cache, in electronic, magnetic, optical, printed, or other format used to store information. Users activate computer programs or network resources to create "processes" which include both the general operation of the computer program along with specific operating characteristics determined by input variables and its environment.

Concepts described below may be further explained in one of more of the co-filed patent applications entitled HELP UTILITY FUNCTIONALITY AND ARCHITECTURE Ser. No. 11/999,906, METHOD AND SYSTEM FOR GRAPHICALLY INDICATING MULTIPLE DATA VALUES Ser. No. 11/999,853, SYSTEM AND METHOD FOR DATABASE INTEGRITY CHECKING Ser. No. 11/999,856, METHOD AND SYSTEM FOR DATA SOURCE AND MODIFICATION TRACKING Ser. No. 11/999,888, PATIENT-CENTRIC HEALTHCARE INFORMATION MAINTENANCE Ser. No. 11/999,874, EXPORT FILE FORMAT WITH MANIFEST FOR ENHANCED DATA TRANSFER Ser. No. 11/999,867, GRAPHIC ZOOM FUNCTIONALITY FOR A CUSTOM REPORT Ser. No. 11/999,932, METHOD AND SYSTEM FOR SELECTIVE MERGING OF PATIENT DATA Ser. No. 11/999,859, METHOD AND SYSTEM FOR PERSONAL MEDICAL DATA DATABASE MERGING Ser. No. 11/999,772, METHOD AND SYSTEM FOR SETTING TIME BLOCKS Ser. No. 11/999,968, METHOD AND SYSTEM FOR ENHANCED DATA TRANSFER Ser. No. 11/999,911, COMMON EXTENSIBLE DATA EXCHANGE FORMAT Ser. No. 11/999,871, METHOD OF CLONING SERVER INSTALLATION TO A NETWORK CLIENT Ser. No. 11/999,876, METHOD AND SYSTEM FOR QUERYING A DATABASE Ser. No. 11/999,912, METHOD AND SYSTEM FOR EVENT BASED DATA COMPARISON Ser. No. 11/999,921, DYNAMIC COMMUNICATION STACK Ser. No. 11/999,934, SYSTEM AND METHOD FOR REPORTING MEDICAL INFORMATION Ser. No. 11/999,878, METHOD AND SYSTEM FOR MERGING EXTENSIBLE DATA INTO A DATABASE USING GLOBALLY UNIQUE IDENTIFIERS Ser. No. 11/999,947, METHOD AND SYSTEM FOR ACTIVATING FEATURES AND FUNCTIONS OF A CONSOLIDATED SOFTWARE APPLICATION Ser. No. 11/999,880, METHOD AND SYSTEM FOR CONFIGURING A CONSOLIDATED SOFTWARE APPLICATION Ser. No. 11/999,894, METHOD AND SYSTEM FOR DATA SELECTION AND DISPLAY Ser. No. 11/999,896, METHOD AND SYSTEM FOR ASSOCIATING DATABASE CONTENT FOR SECURITY ENHANCEMENT Ser. No. 11/999,951, METHOD AND SYSTEM FOR CREATING REPORTS Ser. No. 11/999,851, METHOD AND SYSTEM FOR CREATING USER-DEFINED OUTPUTS Ser. No. 11/999,905, DATA DRIVEN COMMUNICATION PROTOCOL GRAMMAR Ser. No. 11/999,770, HEALTH-CARE MANAGEMENT SYSTEM HAVING IMPROVED PRINTING OF DISPLAY SCREEN INFORMATION Ser. No. 11/999,855, and METHOD AND SYSTEM FOR MULTI-DEVICE COMMUNICATION Ser. No. 11/999,866, the entire disclosures of which are hereby expressly incorporated herein by reference. It should be understood that the concepts described below may relate to diabetes management software systems for tracking and analyzing health data, such as, for example, the Accu-Chek® 360° product provided by Roche Diagnostics. However, the concepts described herein may also have applicability to apparatuses, methods, systems, and software in fields that are unrelated to healthcare. Furthermore, it should be understood that references in this patent application to devices, meters, monitors, pumps, or related terms are intended to encompass any currently existing or later developed apparatus that includes some or all of the features attributed to the referred to apparatus, including but not limited to the Accu-Chek® Active, Accu-Chek® Aviva, Accu-Chek® Compact, Accu-Chek® Compact Plus, Accu-Chek® Integra, Accu-Chek® Go, Accu-Chek® Performa, Accu-Chek® Spirit, Accu-Chek® D-Tron Plus, and Accu-Chek® Voicemate Plus, all provided by Roche Diagnostics or divisions thereof.

Turning now to the figures, FIG. 1 depicts an exemplary embodiment of a homecare system 100 and healthcare system 200 connected via a WAN 150 for monitoring data. Systems 100, 200 each comprise a computing device, shown here in the form of computers 102, 202 having processing units, system memory, display devices 114, 214, and input devices 112, 212, 110, 210, 106. Healthcare computer 202 may be, but is not necessarily, acting as a server. Furthermore, while only two computers 102, 202 are shown, many more computers may be part of the overall system.

While standard input devices such as mice 110, 210 and keyboards 112, 212 are shown, systems 100, 200 may comprise any user input device. By example, infrared (IR) dongle 106 is coupled to each of computers 102, 202. IR dongle 106 is configured to send and receive IR transmissions from health management device 104. Computers 102, 202 include software applications configured to receive data from health management device 104 via IR dongle 106 or otherwise. While the use of IR and IR dongles is disclosed herein for the transmission of data between health management device 104 and computers 102, 202, any other method of wireless transmission is also envisioned, including but not limited to RF. While communications are discussed that make use of dongle 106, the present disclosure is intended to cover internal device hardware having the functionality attributed to dongle 106. Systems 100, 200 include health management software (not shown) configured to receive medical information from one or more of input devices 112, 212, 110, 210, 106. Health management devices 104 are described herein as meters, but could also be a PDA, therapeutic pump, combinations thereof, or other devices that store medical data thereon. Medical information may include blood glucose values, A1c values, Albumin values, Albumin excretion values, body mass index values, blood pressure values, carbohydrate values, cholesterol values (total, HDL, LDL, ratio) creatinine values, fructosamine values, HbAl values, height values, insulin dose values, insulin rate values, total daily insulin values, ketone values, microalbumin values, proteinuria values, heart rate values, temperature values, triglyceride values, weight values, and any other medical information that is desired to be known.

Figure 2:
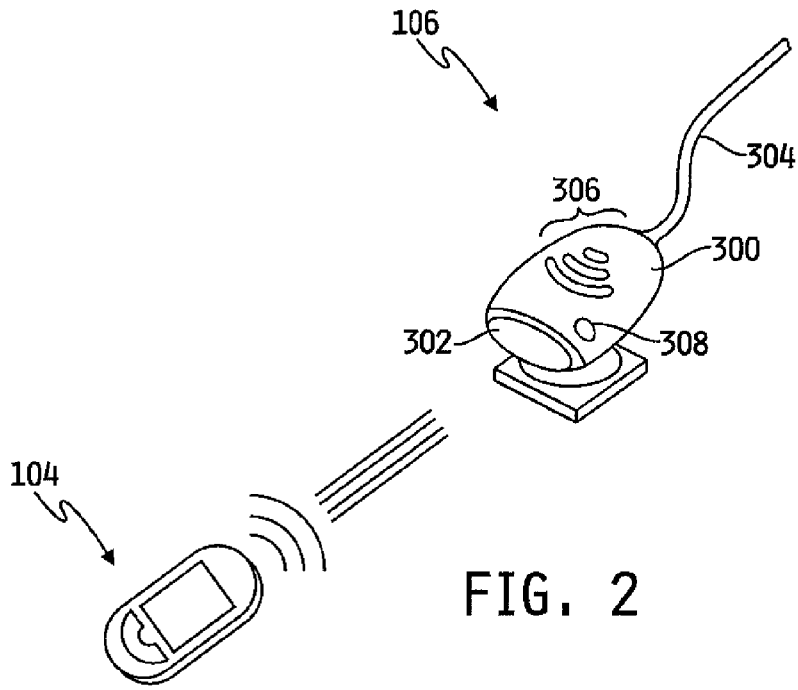
FIG. 2 is a perspective view of a dongle that is part of the systems of FIG. 1.
Figure 3:
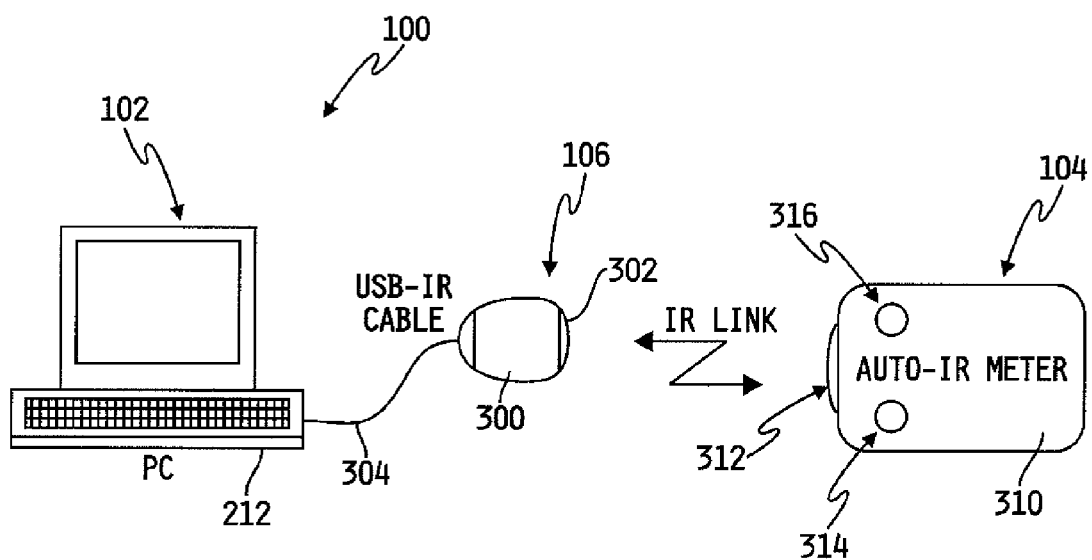
FIG. 3 is a perspective view of a medical device that is part of the systems of FIG. 1.

IR dongle 106, shown in FIG. 2, includes housing 300, IR transmission window 302, and interface cable 304. Housing 300 is sized and shaped to contain IR producing and receiving circuitry therein. IR transmission window 302 is disposed on one side of housing 300 and allows the transmission of IR signals therethrough. Interface cable 304, shown as a USB cable, allows IR dongle 106 to functionally couple to computers 102, 202. Housing 300 also includes reception indicator 306 and communication indicator 308 thereon. Reception indicator 306 provides an indication of reception and the strength of the signal being received from any health management device 104 within range. Reception indicator 306 further allows a user to adjust the positioning of health management device 104 and receive feedback, such as, for example, the display of more or fewer reception "bars," to effect suitable positioning for data transfer. Communication indicator 308 provides an indication of when data is being transmitted between IR dongle 106 and health management device 104.

Health management device 104 may include a housing 310 having an IR window 312, an "IR detected" LED 314, and a "good link" LED 316. IR window 312 is similar to IR transmission window 302 and permits transmission of IR signals therethrough. "IR detected" LED 314 is similar to reception indicator 306 and provides an indication of whether a compatible dongle 106 is detected within range. "Good link" LED 316 is similar to communication indicator 308 and indicates that the IR signal from dongle 106 is suitable for sustaining or is transacting data transfer. While indicators 316, 314, 306, 308 are described as being present on both dongle 106 and health management device 104, embodiments are envisioned wherein indicators would only be present on one of dongle 106 and health management device 104.

In use, dongle 106, when not transmitting data, emits a beacon. The beacon is a repetitive link command that is sent out until either a successful IR link is established with health management device 104 or the software running on computer 102, 202 is shut down. Although the software is described herein for operation on a computer (e.g., desktop, laptop or tablet), it should be understood that the principles of the invention may be embodied in software for operation on various devices, including but not limited to personal digital assistants ("PDAs"), infusion pumps, blood glucose meters, cellular phones, or integrated devices including a glucose measurement engine and a PDA or cellular device. Furthermore, dongle 106 may have an instance of the software running on itself.

Whenever health management device 104 is turned on and not transmitting with dongle 106, the IR communication portion of health management device 104 is in a listening mode. Health management device 104 is listening for the beacon from dongle 106. Listening mode is a mode of reduced power draw relative to a data transmission mode to prolong battery life while still being able to detect dongle 106. Listening involves periodic scanning for or otherwise attempting to sense the presence of the beacon. Upon "hearing" the beacon, health management device 104 recognizes the beacon and wakes up to an active state. Transition from listening mode to the active state in one present embodiment of the invention takes less than five seconds. Health management device 104 then emits data necessary for a handshaking protocol in which health management device 104 and dongle 106 exchange data to ensure that a proper device 104, 106 is on the receiving end of their respective transmissions, to ensure that the other device is prepared to communicate, and to coordinate the start of data transfer.

Once handshaking indicates that proper devices are present, health management device 104 commences sharing any information that is desired to be shared with dongle 106. When the data exchange is being effected, communication indicator 308 and "good link" LED 316 are illuminated to indicate that a proper link has been established. Accordingly, a user is provided with visual feedback that health management device 104 is suitably positioned and that data transfer is occurring. When a user sees communication indicator 308 and/or "good link" LED 316 turn off, the user knows that communication has completed and that health management device 104 can be moved away from dongle 106 without fear that such moving will negatively impact data transmission. Embodiments are envisioned where communication indicator 308 and "good link" LED 316 flash as data is exchanged.

During all times that the beacon is received by health management device 104, "IR detected" LED 314 is illuminated. During all times that dongle 106 detects health management device 104, reception indicator 306 is illuminated. Reception indicator 306 includes the illumination of one or more "bars" or other intensity indicators to indicate the strength of the received signal. A greater number of illuminated bars indicates a stronger signal. Similarly, "IR detected" LED 314 can illuminate in more than one color. Red illumination of "IR detected" LED 314 indicates a poor signal. Yellow illumination of LED 314 indicates a medium strength signal. Green illumination of LED 314 indicates a high strength signal. Alternatively, LED 314 may be binary such that there is only one illumination color. In such embodiments, illumination indicates a satisfactory signal and a lack of illumination indicates a lack of a satisfactory signal. Suitable location of health management device 104 in the present embodiment includes line of sight positioning such that IR signals can travel between health management device 104 and dongle 106 via IR transmission window 302 and IR window 312. Embodiments are also envisioned where instead of, or along with, visual indices 308, 316, 306, 314, audio indices are provided. Such audio indices could be, for example, a first beep to indicate the start of data transmission, multiple beeps to indicate completion of data transmission, and multiple beeps that change in frequency to indicate the strength of signal being received. Such audio indices provide the functionality of visual indices 308, 316, 306, 314 to visually impaired users. Similarly, other sensory indicators (e.g., vibration) are envisioned.

Figure 4:
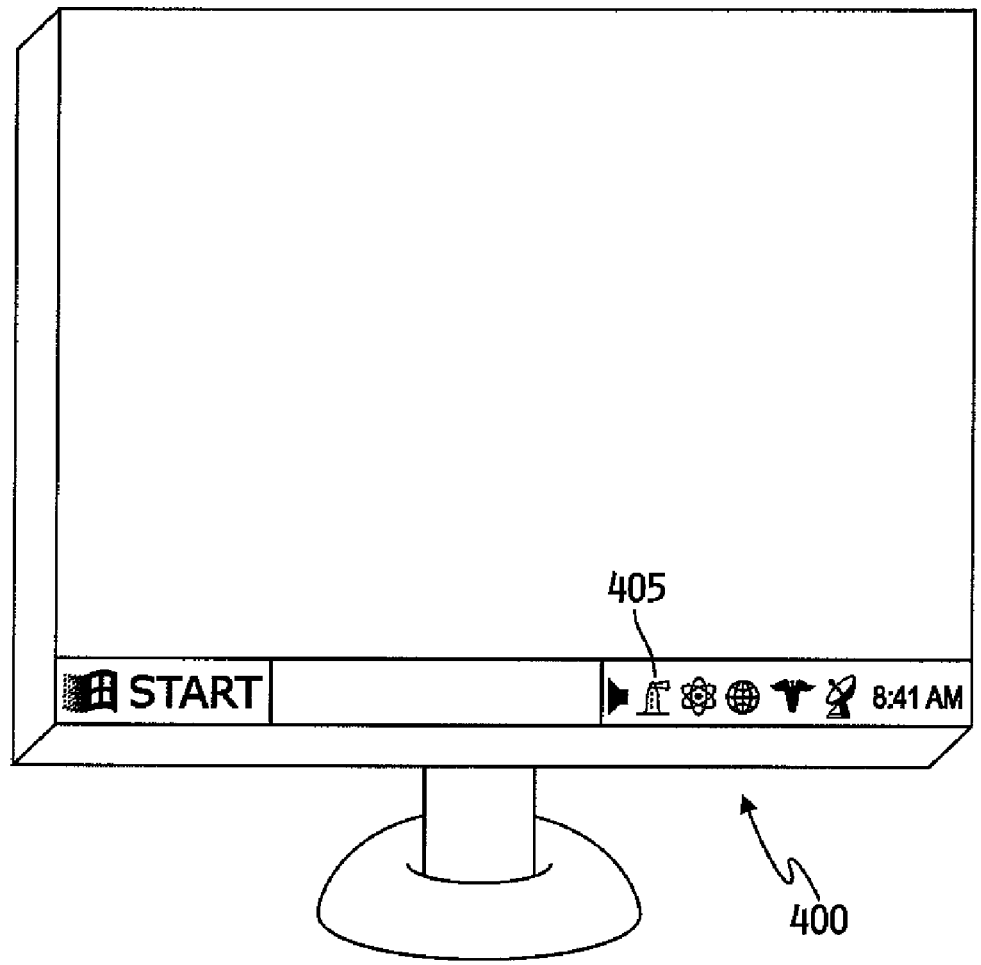
FIG. 4 is a screenshot showing a system tray having an icon for a first piece of software running on the system of FIG. 1.
Figure 5:
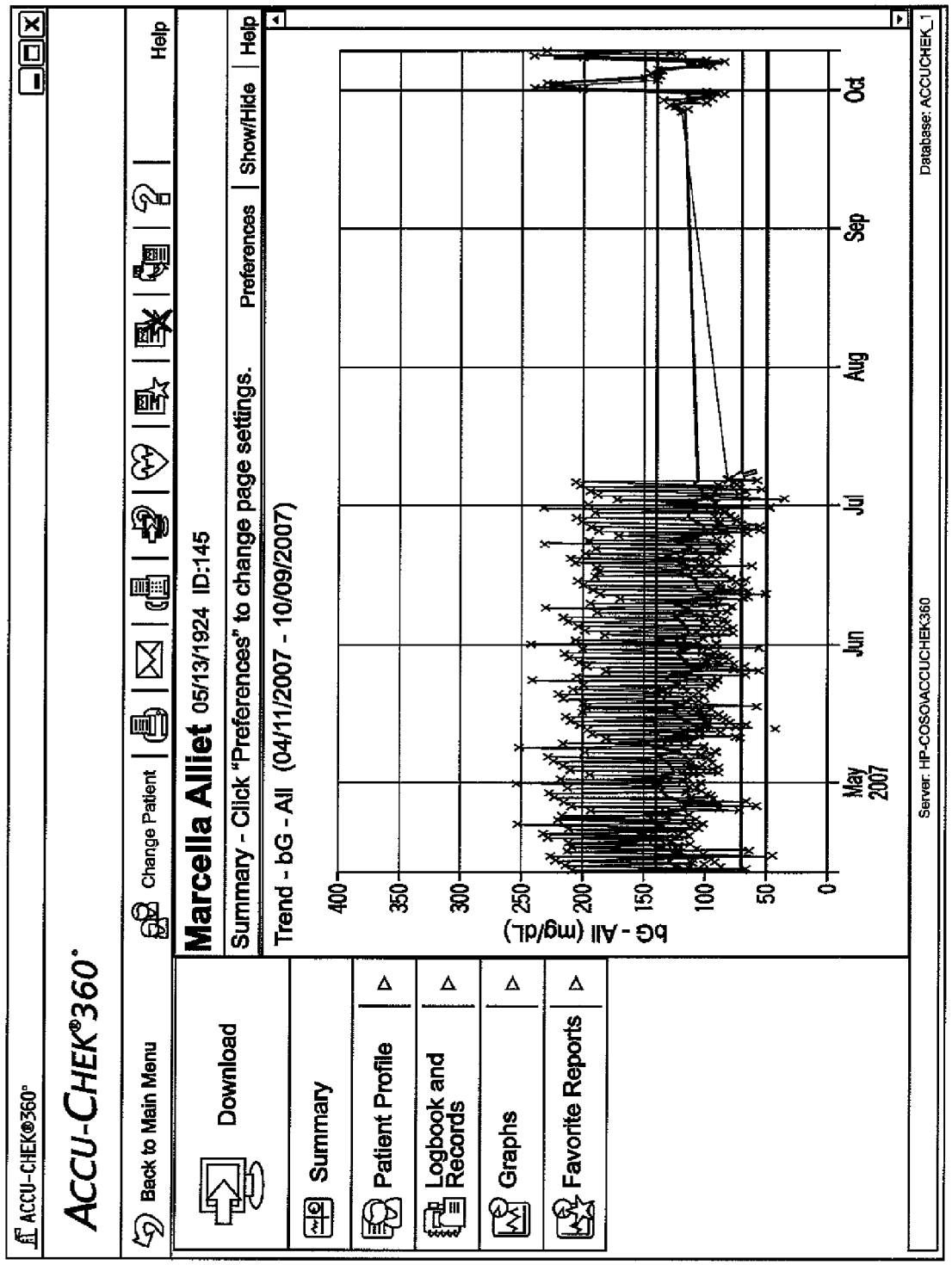
FIG. 5 is a screenshot of a second piece of software running on the system of FIG. 1.

Software 400 runs on computers 102, 202 and waits for detection of health management device 104 via dongle 106. Software 400, represented by icon 405, FIG. 4, in the system tray of computers 102, 202, is loaded automatically on startup and runs in the background to operate dongle 106 and receive indications of the presence of health management device 104. Upon detection of health management device 104, software 400 invokes a related piece of software 410, FIG. 5, that is suitable for receiving and displaying data therefrom. Software 410 either automatically accepts and downloads data from health management device 104, optionally storing the data in a database in association with the patient, or it prompts a user to ask if data from health management device 104 should be downloaded. In embodiments where the data is automatically downloaded, it should be appreciated that such downloading occurs without any user interaction with computers 102, 202. In this automatic embodiment, software 400 is loaded automatically on startup of computers 102, 202 and downloading occurs upon detection of health management device 104. Thus, downloading from health management device 104 is effected with zero manipulation of and zero input to (e.g., zero "clicks" of a mouse) computers 102, 202, provided they are running. In another embodiment, software 400 may be configured to request user authorization/verification of the pending download of data (e.g., via a single "click" of a mouse). Software 410 can also be configured such that reports of the newly downloaded data are presented automatically. Accordingly, computers 102, 202 are able to produce reports with zero clicks and zero interaction with input devices 110, 112, 210, 212. In addition to zero-click downloads to computers 102, 202, downloads may be similarly performed to produce output reports via other devices such as printers, faxes, or e-mail messages. Output devices such as printers and faxes may be configured to automatically produce a hardcopy or report of the downloaded data. Further description of this reporting function for use with the concepts of the present invention is disclosed in the co-filed patent application entitled SYSTEM AND METHOD FOR REPORTING MEDICAL INFORMATION (Roche-P0045) which was previously incorporated herein.

Automatic downloading from health management device 104 is also accomplished in that a device identifier is transmitted with medical data from health management device 104 to dongle 106. The device identifier allows software 410 to determine the individual with whom the incoming data is to be associated. The data may then automatically be downloaded and stored in an appropriate database in association with the corresponding patient. Accordingly, software 410 does not need to be told with which patient to associate the data in systems 100, 200 that service multiple users. The association of a patient to a particular health management device 104 and device identifier is performed the first time that the device interfaces with the installation instance of software 410. It should be appreciated that a particular health management device 104 may not have interfaced with a particular computer 102, 202 and yet the health management device 104 may be recognized thereby. If health management device 104 has previously interfaced with a computer 102, 202 that is networked and/or shares database information with the computer 102, 202 now being used, the information sharing over the network allows recognizing of health management device 104. The device identifier can also identify the type of device that is to be sending the data. Accordingly, differences in device data structures can be known, detected, and compensated for.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The invention claimed is:

1. A medical data transmission system including:
 a dongle configured to wirelessly receive medical data via a signal; the dongle including an externally perceptible indicator of the strength of signal reception;
 a device configured to generate health data; the device being capable of generating the signal; and
 a processor configured to execute instructions to effect automatic data transfer upon detection of a signal of sufficient strength for data transfer.

2. The system of claim 1, wherein the dongle further includes an externally perceptible indicator of data transmission.

3. The system of claim 1, wherein the device is a medical device.

4. The system of claim 1, wherein the indicator includes a set of selectively illuminated lights.

5. The system of claim 1, wherein the dongle includes an emitter that emits a beacon to be detected by the medical device.

6. The system of claim 5, wherein the beacon, when detected by the medical device causes the device to attempt to engage in a handshaking operation with the dongle.

7. The system of claim 1, wherein the dongle is integrated into the medical device, the medical device having a glucose measurement engine therein.

8. A medical data transmission system including:
 a dongle configured to wirelessly receive medical data via a signal; the dongle including an externally perceptible indicator of the strength of signal reception, and
 a device configured to generate health data the device being capable of generating the signal, the indicator including:
  a set of selectively illuminated lights, and
  a set of intensity indicators such that a greater number of activated intensity indicators indicates a greater signal strength than a signal strength indicated by a smaller number of activated intensity indicators.

9. The system of claim 8, wherein the set of selectively illuminated lights is also the set of intensity indicators.

10. The system of claim 8, wherein the dongle further includes an externally perceptible indicator of data transmission.

11. The system of claim 8, wherein the dongle includes an emitter that emits a beacon to be detected by the device.

12. The system of claim 11, wherein the beacon, when detected by the medical device causes the device to attempt to engage in a handshaking operation with the dongle.

13. The system of claim 8, wherein the dongle is integrated into the medical device, the medical device having a glucose measurement engine therein.

14. A medical data transmission system including:
 a medical data device configured to wirelessly communicate medical data to a receiver via a data signal in an active state; the medical device having a listening mode in which the device monitors for a beacon signal emitted by the receiver and the device switches out of the listening mode within five seconds of detecting the beacon signal.

15. The system of claim 14, wherein the listening mode is a mode of decreased power consumption relative to the active state.

16. The system of claim 14 wherein the medical device includes an indicator that indicates when the beacon signal is detected.

17. The system of claim 14, wherein the medical device includes an indicator that indicates when the device is communicating with the receiver.

* * * * *